United States Patent [19]
Fishbein et al.

[11] Patent Number: 5,104,659
[45] Date of Patent: Apr. 14, 1992

[54] COMPOSITIONS, DEVICES AND METHOD FOR CONTROLLING INSECTS

[75] Inventors: Richard Fishbein, Skillman; Joseph Cannelongo, Piscataway; Richard B. Toothill, Warren, all of N.J.

[73] Assignee: American Cyanamid Company, Stamford, Conn.

[21] Appl. No.: 615,611

[22] Filed: May 31, 1984

[51] Int. Cl.$^5$ .................. A01N 25/34; A01N 57/00; A01N 57/10; A01N 37/34; A01N 33/02; A61K 31/74

[52] U.S. Cl. .................................. 424/411; 514/119; 514/144; 514/520; 514/648

[58] Field of Search ............... 424/28, 27, 411, 78; 514/119, 144, 520, 648

[56] References Cited

U.S. PATENT DOCUMENTS

| | | | |
|---|---|---|---|
| 3,705,938 | 12/1972 | Hyman et al. | 424/19 |
| 3,864,468 | 2/1975 | Hyman et al. | 424/29 |
| 3,904,746 | 9/1975 | Aries | 424/28 |
| 3,944,662 | 3/1976 | Miller, Jr. et al. | 424/19 |
| 4,150,109 | 4/1979 | Dick et al. | 424/28 |
| 4,193,986 | 3/1980 | Cox | 424/28 |
| 4,265,876 | 5/1981 | Feakins | 424/28 |
| 4,310,509 | 1/1982 | Berglund et al. | 424/28 |
| 4,320,113 | 3/1982 | Kydonieus | 424/27 |
| 4,348,321 | 9/1982 | McDaniel, Jr. et al. | 424/28 |
| 4,362,722 | 12/1982 | Stubbs | 514/80 |
| 4,536,388 | 8/1985 | Pearce, III | 424/28 |
| 4,543,247 | 9/1985 | von Bittera et al. | 424/27 |
| 4,544,547 | 10/1985 | von Bittera et al. | 424/28 |
| 4,795,075 | 3/1986 | Miller | 424/28 |

FOREIGN PATENT DOCUMENTS 2307466 12/1976 France .................................. 424/28

OTHER PUBLICATIONS

*The Merck Index*, 10th Ed., Abstract #s 3210, 6204, 2054, 4034, 3933, 2763, 2763, 7041, 2855, 4107, 2753 (1983).

*Primary Examiner*—Frederick E. Waddell
*Assistant Examiner*—Raymond J. Henley, III
*Attorney, Agent, or Firm*—John W. Hogan, Jr.

[57] ABSTRACT

The present invention relates to novel insecticidal coating compositions comprising insecticides, such as pyrethroids or mixtures of insecticides, such as pyrethroids and organophosphates, and a vinyl dispersion which is a fluid suspension of a vinyl dispersion resin in a liquid plasticizer system. Additionally, devices coated with said compositions and method for the control of insects are presented.

17 Claims, No Drawings

COMPOSITIONS, DEVICES AND METHOD FOR CONTROLLING INSECTS

BACKGROUND OF THE INVENTION

The present invention relates to compositions, devices and method for controlling insects. Many recently-developed techniques used for the control of insects involve slow-release pesticide technology. The use of pest strips, collars, bands, and tags which have an insecticide contained throughout the substrate of the final device are described in U.S. Pat. Nos. 3,318,679; 3,944,662; 3,765,200; 3,942,480 and more recently, U.S. Pat. No. 4,195,075 which describes an insect-control device containing an insecticidally-active isomer of α-cyano-3-phenoxy-benzyl-α-isopropyl-4-chlorophenylacetate. One common feature of these devices is that they contain a pesticide throughout the substrate of said device.

Additionally, it appears the types of pesticides which are suitable for use in these devices is limited. A problem long-associated with these various devices is the method of preparation that frequently restricts the pesticide to be incorporated. Thus, only pesticides which are stable to the manufacturing process such as extrusion, injection molding, and the like are used. Also, incorporation of pesticides in such devices is limited due to interference of active ingredient with the formation of the final device, as for example, interference with the polymerization process. For example, since the final device contains the pesticide within the matrix material, a homogenous concentration of the pesticide must be present throughout the entire device in order for long term yet efficacious release of pesticide to occur. But often pesticide residues result with such devices that must be disposed. While several devices of this type are currently available, none contains combinations of pesticidally-active ingredients. Compositions of advantage for such pesticidal uses are disclosed in U.S. Pat. No. 4,340,608. In that patent, a phenoxybenzyl ester of a spirocarboxylic acid, a synthetic pyrethroid, with other insecticides for the control of insect pests is described. Compositions containing synthetic pyrethroids with other insecticides will become more desirable in the future, as insects begin developing resistance to these pyrethroids, a phenomenon which is already being reported. Devices containing such combination compositions will be beneficial for the control of insects.

SUMMARY OF THE INVENTION

The present invention provides insecticidal coating compositions useful in coating devices for providing effective insecticidal protection. These compositions are comprised of a vinyl dispersion containing insecticides, preferably a pyrethroid insecticide and an organophosphate.

The objects of the present invention, therefore, are to provide devices and compositions for controlling insects which deliver effective amounts of insecticides; contain lower amounts of insecticidal components than currently available devices; allow the incorporation of wide varieties of insecticides, both alone and in combination; have reduced residues of insecticide upon completion of use; are readily prepared; minimize the problems associated with processing and fabricating devices containing temperature labile insecticides through the matrix; provide a means of delivering a synthetic pyrethroid in combination with other insecticides to control insects which have developed resistance to pyrethroids; and provide a means of altering the release rate of insecticide from the device.

Further, another object of this invention is to provide a device that may be molded, such as insecticidal ear tags, wherein said device is coated or partially coated with the composition of the present invention and wherein said device may or may not have another insecticide located throughout its substrate, and a method for controlling insects in a localized environment by utilizing the devices, for instance, ear tags, of the present invention. These and further objects will become apparent by the more detailed description of the invention that follows.

DESCRIPTION OF THE INVENTION

The present invention relates to insecticidal coating compositions comprising 3% to 30%, by weight, of an insecticide or mixture of insecticides; and about 70% to 97% of a vinyl dispersion wherein said vinyl dispersion is a fluid suspension of a vinyl dispersion resin, said resin having an average particle size of about 0.75 to 1.6 microns, characterized by inherent viscosities, as determined by ASTM D1243, of about 0.80 to 1.20 and curing temperatures of about 20° C. to 180° C., and said vinyl dispersion resin is in a liquid plasticizer system that optionally contains up to 27% (1% to 27%) of additives such as stabilizers, fillers, pigments, colorants, blowing agents, adhesion promoters, such as a carboxyl-terminated PVC copolymer, B-stage phenolics, nitrile phenolics, nitrile latex/borated casein systems or derivatives of natural resins.

Plasticizers suitable for use in vinyl dispersions are usually esters, such as esters of long-chain alcohols with aromatics, like phthalic anhydride and straight-chain dibasic acids such as sebacic and adipic acids, or phosphoric acids. Further, polyesters such as those based on propylene glycol and adipic acid, benzoic acid, trimellitic acid and epoxies such as epoxidized soybean oil may be used. Plasticizers normally comprise about 15% to 40%, on a weight basis, of the vinyl dispersion, and may be employed alone or within an organic solvent or aqueous solvent system containing surfactants.

It has been found that vinyl dispersions, as described, are uniquely suitable for applying effective amounts of a wide variety of insecticides, such as synthetic pyrethroids, carbamates, chlorinated hydrocarbons and even temperature labile organophosphate insecticides, alone or in combination, to a variety of devices which are used to control insects in localized environments, such as those used to control insect pests on animals.

It has also been found that insect control devices prepared by utilizing the novel coating compositions of the present invention containing synthetic pyrethroids with other selected insecticides are highly effective for the total control of insects, including resistant insect strains.

Devices currently in use for this purpose, such as bands, collars and tags, have the insecticidal component distributed throughout the substrate (matrix) of a molded device, and such devices usually contain only one active ingredient. Additionally, they are limited to those insecticides which are stable at the temperatures encountered during fabrication procedures, such as injection molding or extrusion, where temperatures of 160° C. or greater are commonly employed.

The insect control devices of the present invention containing the insecticide in the coating composition may be prepared at much lower temperatures, as low as about 20° C. The greatly-reduced processing temperatures allow the incorporation of active ingredients which are thermally unstable at elevated temperature. Examples of insecticides which may now be incorporated in such devices are dimethoate, dibrom, and chlorfenvinphos, illustrated in Table I. The decomposition points of these insecticides, as determined by differential scanning calorimetry (DSC), is below the 160° C. minimum temperatures encountered during extrusion or injection molding of plasticized PVC, and as such, these compounds can now be effectively incorporated in the present devices for control insect pests.

TABLE I

| Stability of organophosphates by DSC | |
|---|---|
| Organophosphate | Onset of Decomposition (°C.) |
| Dimethoate | 105 |
| Temephos | 142 |
| Dibrom | 103 |
| Chlorfenvinphos | 157 |
| Tetrachlorvinphos | 190 |

The utilization of these types of insecticides is of particular interest because insects have developed resistance to pyrethroids, as illustrated in Table II. Thus, the incorporation of other effective insecticides into devices containing synthetic pyrethroids, such as cattle ear tags containing flucythrinate, fenvalerate, permethrin, cypermethrin and cypothrin, is desirable in order to provide control of those insects which have developed resistance to pyrethroids.

Furthermore, the incorporation of other insecticides can increase the initial effectiveness of devices containing pyrethroid-type compounds. The usual initiation periods of devices containing pyrethroids within the matrix, when tested in vivo in cattle, are shown in Illustration I below.

TABLE II

| Effectiveness of some insecticides against pyrethroid resistant flies | |
|---|---|
| Insecticide | LD$_{50}$ Micrograms/pyrethroid resistant female flies |
| Dimethoate | 0.0448–0.0715 |
| Dibrom | 0.0242–0.0337 |
| Chorfenvinphos | 0.1869–0.2626 |
| Malathion | 4.4757–6.9321 |
| Chlorpyrifos | 0.3144–1.486 |
| Chlordimeform | >8.0 |
| Coumaphos | >21.0 |
| Dicapthon | 0.2649–0.6539 |
| Isodimethoate | 0.6136–0.8801 |
| Famphur | 0.1359–8.448 |
| Endosulfan | 0.3518–0.5009 |
| Methomyl | 0.5027–0.6807 |
| Diazinon | 4.0626–6.2101 |
| Piperonyl butoxide | 2.725–3.7726 |

ILLUSTRATION I

| Insect | Days after treatment | 7.5% Flucythrinate matrix tag (2 per animal) | Permethrin tape |
|---|---|---|---|
| Stable/ | 0 | — | — |
| fly | 6 | — | 0 |
| | 7 | — | 90.9 |
| | 10 | 92.9 | 78.6 |
| | 17 | 100.0 | 37.5 |
| | | | 8% Fenvalerate matrix tag (2 per animal) |
| Horn fly | 1 | 42.5 | 40.4 |
| | 2 | 67.5 | 30.9 |
| | 3 | 93.1 | 46.9 |
| | 14 | 97.0 | 77.4 |

It has been found, in a chamber screening evaluation that cattle ear tags coated with a composition disclosed in the present invention, containing 7.5%, on a weight basis, of the synthetic pyrethroid, flucythrinate, and 7.5%, on a weight basis, of dimethoate are highly effective for the initial (six day) control of both flucythrinate resistant flies and non-resistant flies as demonstrated in Table III.

TABLE III

| | % Fly mortality - six days | |
|---|---|---|
| | Non-resistant strain | Resistant strain |
| Control | 2 | 2 |
| Positive control/ petri dish 0.05% flucythrinate | 77 | 4 |
| Molded flucythrinate tag | 8 | 3 |
| Dimethoate plus flucythrinate coated tag | 89 | 85 |

It also should be recognized that the insecticidal devices coated with the present compositions provide other advantages over conventional devices because the present devices can contain not only synthetic pyrethroids, but other insecticides such as halogenated hydrocarbons, carbamates and organophosphates alone or in combinations, and as such, these devices are already not limited to only thermally stable insecticides.

Furthermore, insecticidal devices already containing an active ingredient within the substrate of said devices, such as the matrix material of molded ear tags, may be coated or partially coated with the present coating compositions in order to introduce other insecticides or mixtures of insecticides to the device.

Insect control devices prepared utilizing present novel coating compositions use less insecticide than non-coated devices because the insecticidally-active ingredients are found only in the coating representing only 10% to 40% of the total weight of the device. Thus, upon completion of use, residual insecticide in the device will be lower than found in devices having insecticide dispersed throughout the matrix, making disposal of such devices easier because little or no insecticidal residues will be left.

Additionally, the present devices coated with the compositions of the invention provide a greater variety in altering the release rate from the coating composition. For instance, a choice of primary and secondary plasticizers, fillers, polymers and co-polymers may alter release as well as concentration of active ingredient and thickness of the coating. Bleeding agents, such as fatty acids, fatty alcohols, oils and the like may be used. Furthermore, degree of curing of the insecticidal/vinyl dispersion compositions of the present invention may be varied over a temperature range of about 20° C. to 180° C. and the time of curing may be varied from several minutes to several days. These alterations affect the rate of release of the insecticidal active ingredient.

Devices coated and/or partially coated with compositions of the present invention for the control of insects may be readily prepared by admixing, at room temperatures, about 3% to 30%, on a weight basis, of an insecticide or mixture of insecticides, with about 70% to 97%, on a weight basis, of a vinyl dispersion, up to 27%, 1% to 27%, on a weight basis, of additives, such as stabilizers, fillers, pigments, colorants and adhesion agents may be added. This is blended for a sufficient period of time to obtain a homogeneous mixture. The mixture is then deaerated, under reduced pressure, at room temperature. The resulting insecticidal coating composition may then be applied to the surface of a device, such as an ear tag, by dipping, brush application or spraying, and is subsequently cured at a temperature of about room temperature (20° C.) to 180° C. for several minutes to two days, preferably cured at 80° C. to 140° C. for 45 seconds to 20 minutes.

While for convenience the generic names of insecticides have been used in text, a listing of generic names and the corresponding chemical names of several of the preferred insecticides is presented below:

| Generic | Chemical |
|---|---|
| Flucythrinate | (±)-cyano(3-phenoxyphenyl)methyl (+)-4-(difluoromethoxy-α-(1-methylethyl)benzeneacetate |
| Cypothrin | Cyano(3-phenoxyphenyl)methyl spiro-[cyclopropane-1,1'-[1 H]indene]-2-carboxylic acid |
| Fenvalerate | Cyano(3-phenoxyphenyl)methyl 4-chloroalpha-(1-methylethyl)benzene-acetate |
| Permethrin | 3-(Phenoxyphenyl) methyl (±)-cis-, trans-3-(2,2-dichloroethenyl)-2,2-dichloroethenyl)-2,2-dimethyl cyclopropane carboxylate |
| Cypermethrin | ±-Cyano-3-phenoxybenzyl (±)-cis-, trans-3-(2,2-dichlorovinyl)-2,2-dimethyl cyclopropane carboxylate |
| Deltamethrin | (S)-α-Cyano-m-phenoxybenzyl (1R, 3R)-3-(2,2-dibromovinyl)-2,2-dimethylcyclopropanecarboxylate |
| Resmethrin | ({5-(Phenylmethyl)-3-furanyl} methyl-2,2-dimethyl-3-(2-methyl-l-propenyl) cyclopropanecarboxylate |
| Tetramethrin | 1-cyclohexene-1,2-dicarboximidomethyl-2,2-dimethyl-3-(2-methylpropenyl)-cyclopropanecarboxylate (3,4,5,6-tetrahydrophthalimidomethyl (±)-cis-trans-chrysanthemate |
| Flumethrin | Cyano(4-fluoro-3-phenoxyphenyl)-methyl 3-[2-chloro-2-(4-chloro-phenyl)ethenyl]-2,2-dimethylcyclopropanecarboxylate |
| Cyhalothrin | Cyano(3-phenoxyphenyl)methyl 3-(2-chloro-3,3,3-trifluoro-1-propenyl)-2,2-dimethylcyclopropanecarboxylate |
| Fluvalinate | Cyano(3-phenoxyphenyl)methyl N-[2-chloro-4-(trifluoromethyl)phenyl] DL-valinate |
| Dimethoate | O,O-dimethyl S-(N-methylcarbamoyl-methyl)phosphorodithioate |
| Dibrom | 1,2-Dibromo-2,2-dichloroethyl dimethyl phosphate |
| Chlorfenvinphos | 2-Chloro-1-(2,4-dichlorophenyl)-vinyl diethyl phosphate |

The present invention is further illustrated by the following non-limiting examples.

EXAMPLE 1

Preparation of a Coated Cattle Ear Tag

A vinyl dispersion is prepared by stirring 57.3%, on a weight basis, of a vinyl dispersion resin, having an inherent viscosity of 1.20, and an average particle size of 0.75 microns, a curing temperature range of about 120° C. to 180° C., with 28.6%, on a weight basis, of butyl benzyl phthalate. Stirring is continued, and 1.7%, on a weight basis, of Ca/Zn stearate stabilizer is added, followed by the addition of 7.5% flucythrinate (9.45%, 76.8% pure) and 2.86% of epoxidized soybean oil. The resulting homogeneous mixture is deaerated for 15 to 20 minutes at 125 mm/Hg. The resulting mixture is coated on an ear tag template by dipping, and the resulting tag is cured at 148° C. for five minutes.

EXAMPLE 2

Preparation of Insecticidal Coating Composition Containing a Synthetic Pyrethroid and Organophosphate Insecticide Butyl benzyl phthalate, 180 g, is added to a stirred mixture of 300 g of a vinyl resin, having an inherent viscosity of 1.20 and average particle size of 0.95 microns, plus 6 g of Ca/Zn stearate and 9 g of epoxidized soybean oil. To this stirred mixture is added 44.66 g of dimethoate and 55.83 g of flucythrinate (80% pure). The resulting mixture is stirred until homogeneous and deaerated at room temperature overnight at 125 mm/Hg.

EXAMPLE 3

Preparation of Coated Ear Tags Containing a Mixture of Synthetic Pyrethroid and Organophosphate Insecticides Standard 10.5 g ear tags of medium hardness are preheated to 100° C. and dipped into the insecticidal coating composition prepared in Example 2. The resulting coated tags are cured, in an oven, at 90° C. to 100° C. for five to eight minutes, resulting in coated tags containing 1.7 g to 2.86 g (16.2% to 27.3% of total tag weight) of the insecticidal coating composition.

EXAMPLE 4

Comparative Insecticidal Screening Evaluation of Coated Ear Tags Containing Synthetic Pyrethroid and Organo-Phosphate Insecticides and Commercially Available Ear Tags The ear tags are hung in a chamber covered with mesh cloth to keep the flies confined in the 12"×17"×9" space. Each chamber contains a cup of water and a supply of sugar and powdered milk.

At the start of the test, ~100 three to five day old house flies are placed in each chamber. The chambers are kept in a room with the temperature at 82° F. (27.8° C.). The flies are observed daily (except Saturday and Sunday) and mortality is recorded. At the termination of the study, the chambers are placed in a freezer overnight to kill the remaining flies, which are then counted. The percent mortality is calculated based on the number of flies that die during the observation period and the number of flies counted at the end of the study.

The results of these experiments summarized in Table IV demonstrate the improved effectiveness for initial control and control against a resistant strain of flies utilizing ear tags which are prepared with the insecticidal coating compositions of the present invention containing 7.5%, by weight, flucythrinate and 7.5%, by weight, dimethoate (representing an average of 0.34 g total active ingredient per tag) when compared to a tag that contains 7.5%, by weight, flucythrinate throughout the tag (0.78 g active ingredient).

TABLE IV

| | % Fly mortality - six days | |
|---|---|---|
| | Non-resistant strain | Resistant strain |
| Control | 2 | 2 |
| Positive control/ petri dish 0.05% flucythrinate | 77 | 4 |
| Molded flucythrinate tag | 8 | 3 |
| Dimethoate plus flucythrinate coated tag | 89 | 85 |

EXAMPLE 5

Preparation of Coated Ear Tags Containing Insecticides Alone or in Combination

Utilizing the procedure of Examples 1, 2 and 3, insecticidal coated ear tags may be readily prepared utilizing the compositions illustrated in Table V below.

TABLE V

| Ingredient | 1 Wt g | 2 Wt g | 3 Wt g | 4 Wt g |
|---|---|---|---|---|
| Resin (Inherent viscosity 1.20 average particle size 0.95 | 300 | 300 | 300 | 300 |
| Butyl benzyl phthalate | 126.2 | 137.7 | 83.9 | 131.9 |
| Epoxidized soybean oil | 9 | 9 | 9 | 9 |
| Ca/Zn Stearate | 6 | 6 | 6 | 6 |
| Benzophenone (ultra violet stabilizer) | 2 | 2 | 2 | 2 |
| Flucythrinate | 41.3 | — | 53.8 | 26.9 |
| Dimethoate | — | 42.3 | 42.3 | 21.2 |
| Cure Temp.°C./ | 100° C. | 100° C. | 100° C. | 100° C. |
| Time of coated tag | 5 min | 5 min | 5 min | 5 min |

EXAMPLE 6

Preparation of Coated Ear Tags Containing Various Synthetic Pyrethroids in Combination with Various Organophosphate Insecticides (a) A vinyl dispersion is prepared utilizing the procedure of Example 2 and the materials listed in Table VI below.

TABLE VI

| Ingredient | Wt g | % Wt of dispersion |
|---|---|---|
| Resin (Inherent viscosity 1.20 average particle size 0.95 microns | 300 | 49.72 |
| Butyl benzyl phthalate | 180 | 29.82 |
| Epoxidized soybean oil | 9 | 1.49 |
| Ca/Zn Stearate | 6 | 0.99 |
| Benzophenone ultra violet stabilizer | 2 | 0.33 |

(b) Insecticidal coating compositions may then be prepared by addition of the insecticidal compositions illustrated in Table VII below to the vinyl dispersion prepared in 6(a) and blending until homogenous. The resulting mixture is then deaerated at reduced pressure, 125 mm/Hg, for 16 hours, giving the insecticidal coating compositions suitable for preparing coated insect control devices.

(c) Insect control devices, such as ear tags, may then be prepared by coating or partially coating a blank tag or a tag containing insecticide throughout the matrix with the compositions prepared in Example 6(b) and curing the resulting coated tag at 110° C. to 120° C. for five minutes.

TABLE VII

| Pyrethroid | Dimethoate | Dibrom | Chlorfenvinphos | Vinyl dispersion of Example 6 |
|---|---|---|---|---|
| Flucythrinate | 7.5/7.5 | 7.5/7.5 | 7.5/7.5 | 85 |
| Fenvalerate | 7.5/7.5 | 7.5/7.5 | 7.5/7.5 | 85 |
| Cypermethrin | 7.5/7.5 | 7.5/7.5 | 7.5/7.5 | 85 |
| Permethrin | 7.5/7.5 | 7.5/7.5 | 7.5/7.5 | 85 |
| Cypothrin | 7.5/7.5 | 7.5/7.5 | 7.5/7.5 | 85 |
| Deltamethrin | 7.5/7.5 | 7.5/7.5 | 7.5/7.5 | 85 |
| Fluvalinate | 7.5/7.5 | 7.5/7.5 | 7.5/7.5 | 85 |
| (Z)-trans-α-cyano-m-phenoxy-benzyl 3-(β-cyano-styryl)-2,2-dimethylcyclopropanecarboxylate | 7.5/7.5 | 7.5/7.5 | 7.5/7.5 | 85 |

EXAMPLE 7

Insecticidal Evaluation of Coated Tags Containing Various Pyrethroids and Organophosphates Coated ear tags prepared by the procedure of Example 6 are screened for insecticidal effectiveness by suspending each cured coated tag being evaluated in a one-gallon cylindrical container containing 100 three- to-five-day-old flies. These containers also have aqueous milk and sugar solution. Each composition is tested in replicate against a control. The containers are kept in a room maintained at 82° F. (27.8° C.) with the percent mortality determined after 24 hours exposure. The results of these experiments summarized in Table VIII demonstrate the effectiveness of ear tags coated with insecticidal coating compositions of the inventions containing 7.5%, by weight, of a pyrethroid insecticide and/or 7.5%, by weight, of an organophosphate insecticide.

TABLE VIII

| Insecticidal Composition | Average % mortality 24 hours replicated |
|---|---|
| Flucythrinate 7.5% | 61 |
| plus dimethoate 7.5% | 78 |
| Flucythrinate 7.5% | 97 |
| plus dibrom 7.5% | 99 |
| Flucythrinate 7.5% | 1 |
| plus chlorfenvinphos 7.5% | 0 |
| Fenvalerate 7.5% | 59 |
| plus dimethoate 7.5% | 74 |
| Fenvalerate 7.5% | 2 |
| plus chlorfenvinphos 7.5% | 1 |
| Cypermethrin 7.5% | 57 |
| plus dimethoate 7.5% | 62 |
| Cypermethrin 7.5% | 99 |
| plus dibrom 7.5% | 99 |
| Cypermethrin 7.5% | 4 |
| plus chlorfenvinphos 7.5% | 3 |
| Cypothrin 7.5% | 51 |
| plus dimethoate 7.5% | 71 |
| Cypothrin 7.5% | 97 |
| plus dibrom 7.5% | 89 |
| Cypothrin 7.5% | 1 |
| plus chlorfenvinphos 7.5% | 0 |
| Control - None | 1 |

What is claimed is:

1. An insecticidal coating composition comprising: a mixture of about 5% to 10%, by weight, of a pyrethroid insecticide selected from the group consisting of flucythrinate, fenvalerate, cypermethrin and cypothrin; in combination with about 5% to 10%, by weight, of an organophosphate insecticide selected from the group consisting of dimethoate and dibrom; and about 80% to 90% of a vinyl dispersion, wherein said vinyl dispersion contains a fluid suspension of a vinyl dispersion resin having an average particle size of about 0.75 to 1.6 microns, inherent viscosity, as determined by ASTM D1243, of about 0.80 to 1.20, and curing temperature of about 20° C. to 180° C., and a liquid plasticizer.

2. A composition according to claim 1, additionally comprising 1% to 10% additives, wherein said addtives are stabilizers or bleeding agents.

3. A composition according to claim 2, wherein said vinyl dispersion resin has a curing temperature of about 80° C. to 140° C.

4. A device for the control of insects in a localized environment, said device comprising: an insecticidal coating composition and substrate; wherein said insecticidal coating composition contains a mixture of about 5% to 10%, by weight, of a pyrethroid insecticide selected from the group consisting of flucythrinate, fenvalerate, cypermethrin and cypothrin; in combination with about 5% to 10%, by weight, of an organophosphate insecticide selected from the group consisting of dimethoate and dibrom; and about 80% to 90% of a vinyl dispersion, wherein said vinyl dispersion contains a fluid suspension of a vinyl dispersion resin having an average particle size of about 0.75 to 1.6 microns, inherent viscosity, as determined by ASTM D1243, of about 0.80 to 1.20, and curing temperature of about 20° C. to 180° C., and a liquid plasticizer; wherein said insecticide coating composition coats or partially coats said substrate; and wherein said device is molded.

5. A device according to claim 4, additionally comprising 1% to 10% additives, wherein said additives are stabilizers or bleeding agents.

6. A device according to claim 5, wherein said device is an ear tag.

7. An improved device for the control of insects in a localized environment, said device containing an insecticide throughout its substrate, the improvement comprising: coating or partially coating said device with an insecticidal coating composition comprising a mixture of about 5% to 10%, by weight, of a pyrethroid insecticide selected from the group consisting of flucythrinate, fenvalerate, cypermethrin and cypothrin; in combination with about 5% to 10%, by weight, of an organophosphate insecticide selected from the group consisting of dimethoate and dibrom; and about 80% to 90% of a vinyl dispersion, wherein said vinyl dispersion contains a fluid suspension of a vinyl dispersion resin having an average particle size of about 0.75 to 1.6 microns, inherent viscosity, as determined by ASTM D1243, of about 0.80 to 1.20, and curing temperature of about 20° C. to 180° C., and a liquid plasticizer.

8. A device according to claim 7, additionally comprising 1% to 10% of additives, wherein said additives are stabilizers or bleeding agents.

9. A device according to claim 8, wherein said device is an ear tag.

10. A device according to claim 6 or 9, comprising: about 5% to 10%, by weight, of flucythrinate; and about 5% to 10%, by weight, of dimethoate.

11. A device according to claim 6 or 9, comprising: about 5% to 10%, by weight, of flucythrinate; and about 5% to 10%, by weight, of dibrom.

12. A device according to claim 6 or 9, comprising: about 5% to 10%, by weight, of fenvalerate; and about 5% to 10%, by weight, of dimethoate.

13. A device according to claim 6 or 9, comprising: about 5% to 10%, by weight, of fenvalerate; and about 5% to 10%, by weight, of dibrom.

14. A device according to claim 6 or 9, comprising: about 5% to 10%, by weight, of cypermethrin; and about 5% to 10%, by weight, of dimethoate.

15. A device according to claim 6 or 9, comprising: about 5% to 10%, by weight, of cypermethrin; and about 5% to 10%, by weight, of dibrom.

16. A device according to claim 6 or 9, comprising: about 5% to 10%, by weight, of cypothrin; and about 5% to 10%, by weight, of dimethoate.

17. A device according to claim 6 or 9, comprising: about 5% to 10%, by weight, of cypothrin; and about 5% to 10%, by weight, of dibrom.

* * * * *